United States Patent
Starostovic

(10) Patent No.: US 6,381,546 B1
(45) Date of Patent: Apr. 30, 2002

(54) PANEL TESTER AND GRADER

(75) Inventor: Edward J. Starostovic, Stoughton, WI (US)

(73) Assignee: Timberco, Inc., Madison, WI (US)

( * ) Notice: Subject to any disclaimer, the term of this patent is extended or adjusted under 35 U.S.C. 154(b) by 0 days.

(21) Appl. No.: 09/431,865

(22) Filed: Nov. 2, 1999

(51) Int. Cl.$^7$ ................................................. G01N 3/20
(52) U.S. Cl. .............................. 702/36; 702/97; 73/849; 428/119
(58) Field of Search ............................ 702/41, 36, 113, 702/91, 94, 97; 73/849, 851, 852; 428/119, 120, 167, 172

(56) References Cited

U.S. PATENT DOCUMENTS

| | | | |
|---|---|---|---|
| 4,589,288 A | * 5/1986 | Porter et al. | 73/852 |
| 4,708,020 A | * 11/1987 | Lau et al. | 73/852 |
| 4,852,029 A | * 7/1989 | Pope et al. | 702/41 |
| 5,060,516 A | 10/1991 | Lau et al. | 73/602 |
| 5,231,882 A | * 8/1993 | Bertele | 73/852 |
| 5,503,024 A | * 4/1996 | Bechtel et al. | 73/852 |
| 5,699,274 A | * 12/1997 | Starostovic, Jr. | 702/113 |
| 5,804,738 A | * 9/1998 | Bach et al. | 73/849 |
| 6,053,052 A | * 4/2000 | Starostovic | 73/851 |
| 6,055,867 A | * 5/2000 | Dunne et al. | 73/849 |

* cited by examiner

Primary Examiner—Kamini Shah

(74) Attorney, Agent, or Firm—Michael Best & Friedrich LLP

(57) ABSTRACT

There is provided an improved panel tester and grader which is used for determining the strength and stiffness values for individually tested panels. In one aspect of the present invention, an improvement resides in providing an apparatus and method which more accurately determines when a panel is properly located within a test load zone such that certain measurements regarding the panels characteristics may be properly measured. These variables ultimately contribute to the calculated overall strength and stiffness values. Pairs of opposing rolls are provided to process the panels therebetween along a processing line. The opposing rolls each include a groove extending completely around their outer surfaces. The grooves of the opposing rolls are aligned so as to define respective channels extending between the pairs of opposing rolls. Individual location sensors are positioned relative to the channels to determine where the panels are located along the processing line at any given moment. In another aspect of the present invention, an improvement resides in providing a thickness measuring device coupled to the framework to more accurately determine the thickness of each panel travelling through the machine thereby improving the accuracy of the calculated strength and stiffness value of each panel. The opposing rolls are supported by at least two frames wherein at least one frame is movable with respect to the other. As the panels travel between the rolls, the varying thicknesses of the panels will cause the movable frame to move up or down. The thickness measuring device measures this movement which corresponds to the thickness of each panel.

15 Claims, 1 Drawing Sheet

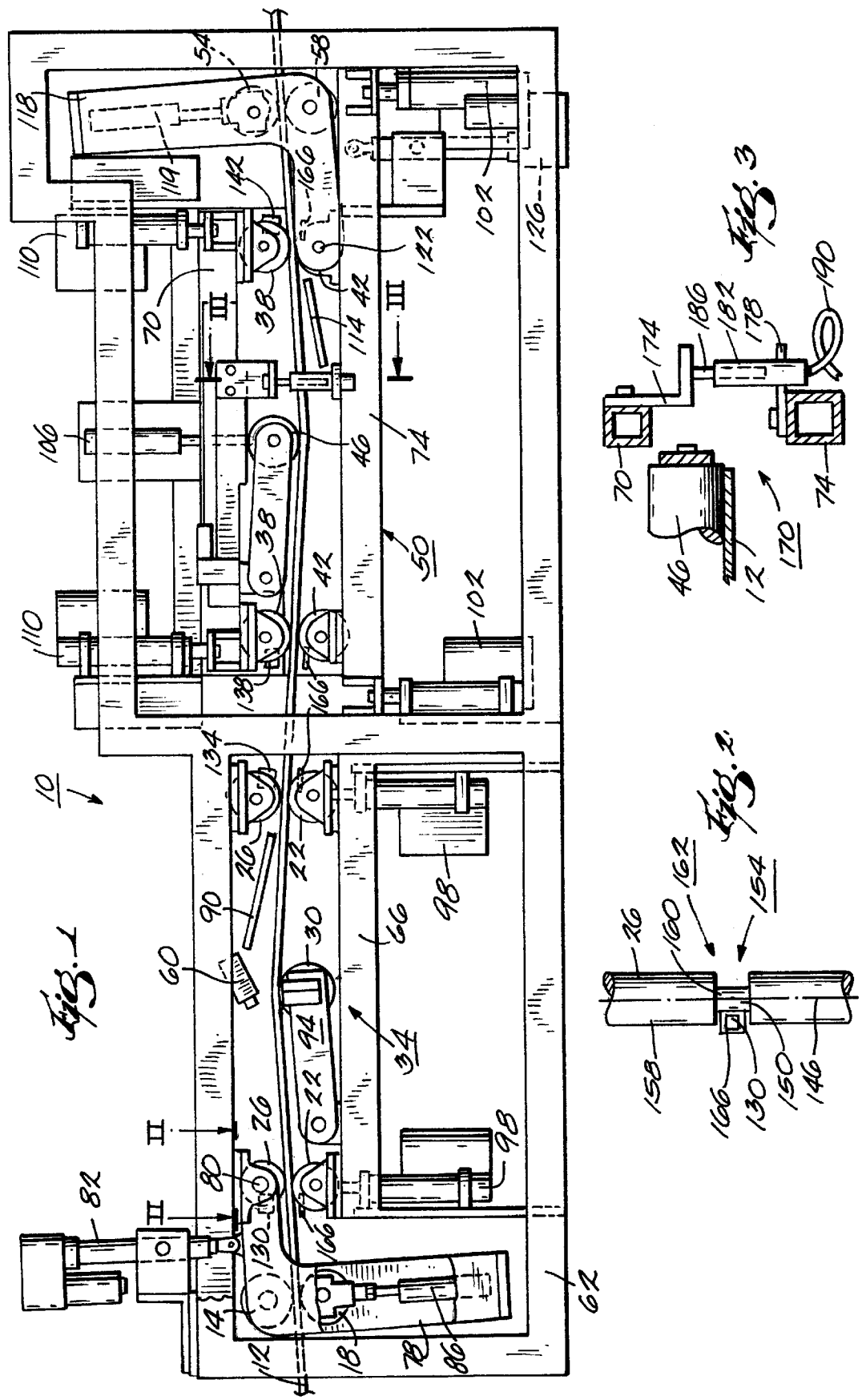

PANEL TESTER AND GRADER

FIELD OF THE INVENTION

The present invention relates generally to nondestructive testing of composite materials or panels, particularly wood based materials, such as plywood, oriented strand board, wafer board, particle board, and the like, to determine the strength and stiffness of such panels.

BACKGROUND OF THE INVENTION

The use and acceptance of composite materials and panels for various applications, such as, building constructions, continues to increase in the market place. As a result, it is becoming increasingly desirable to monitor the strength and stiffness of the panels being produced. This is so because the strength and stiffness of composite materials varies greatly due to the composite nature of the products and the difficulty in achieving uniform strength in the bonding materials used to join the composites together. Moreover, variations in feedstocks and other factors make manufacture of uniformly strong and elastic structures from composite elements difficult and costly.

Nondestructive inspection and testing of materials of all sorts is known. Many of the known methods for performing certain standards tests are manual or static methods. For example, to conduct a concentrated load test, it is known to build a frame with beams simulating joists in a building construction. The beams are spaced apart depending upon the end use and span rating of the panel to be tested. A hydraulically-actuated load is applied to the stationary panel at a specified distance from a non-secured edge and the deflection of the panel is measured by placing a dial-micrometer under the panel at a position opposite the load and reading the deflection on the micrometer scale.

U.S. Pat. No. 4,708,020 to Lau et al., which is incorporated herein by reference, relates to another form of nondestructive inspection and testing of composite panels to determine the strength and stiffness of the panels. More particularly, Lau et al. provide an apparatus and process for correlating end-use strength and stiffness values when the testing is carried out on hot panels. The panels may be tested at one temperature, approaching the press temperature, and the strength and stiffness determined for the end products at another temperature, generally ambient or end-use temperature. Lau et al. also provide a testing machine suitable for in-line testing for determining the strength and stiffness of panel products having different thicknesses. The testing machine of Lau et al. also enables panels to be graded so that rejects can be identified and panels can be separated into grade groups representing different strength and stiffness ranges.

The continuous panel tester of Lau et al. imposes a double reverse bend or "S" shaped configuration on the panels as they pass through the conveyor at line speed. The device of Lau et al. is configured and operated such that either the deflection of each panel may be measured for a specific load, or the load is measured for a particular deflection of each panel.

As set forth in Lau et al., there is provided a first in-feed roll and a last out-feed roll to direct each panel to be tested into and out of the overall continuous panel tester and grader. As also described in Lau et al., a plurality of photo switches along the conveyor line have the function of informing the microprocessor when a panel is in the tester. The photo switches of Lau et al. determine when one panel ends and a second panel commences to pass through the tester so as to ensure that readings from the load cells and temperature sensor represent strength and stiffness figures for one panel. Another feature of Lau et al. is the ability of the panel grader to test panels having different thicknesses by merely selecting the required nominal panel thickness. The microprocessor is programmed to control the necessary equipment to position the rolls of the apparatus to process the panels of the selected nominal thickness. Based on the selected nominal thickness which is inputted to the microprocessor, the microprocessor utilizes information received from the load cells and temperature sensor to calculate the hot strength and stiffness values for each panel and then the microprocessor uses a preprogrammed algorithm to determine the ambient or cold end-use strength and stiffness value for each of the tested panels. Lau et al. do provide that it may be desirable to use a thickness measuring sensor such as a laser sensor or an ultrasonic sensor, which is placed near the in-feed rolls of the panel tester, to obtain a more actual thickness measurement of each panel, as compared to using the selected nominal thickness for each panel, thereby providing for a more accurate calculation of the strength and stiffness properties for each panel.

Despite the increased use of composite materials for all sorts of building constructions and other uses, and the general desire to test the composite materials for strength and stiffness, a need still exists for an improved panel tester and grader which is efficient and economical in its manufacture and use and which also provides improved accuracy in terms of measuring and grading panel like products according to desired strength and stiffness values.

As can be appreciated by those skilled in the art, the many known manual methods for performing certain standards tests for panels or the like are generally labor intensive, slow processing, somewhat costly procedures that can readily lead to error or operator mistakes when trying to determine the strength and stiffness values for panels. Moreover, the known static testing machines do not allow a panel to continually move along the production line during testing, thereby limiting the usefulness of such testing equipment.

Although Lau et al. describe an automatic, continuous panel tester and grader which is in many aspects an improvement over the known manual or static methods, the device of Lau et al. also exhibits several problems. One problem with Lau et al. concerns the bending forces that are applied to the panels as they are fed to and passed out of the panel tester. Although Lau et al. recognize that no significant forces should be applied to the panels that would distort the loading forces of the panels in the "S" shaped path, it has actually been determined according to the present invention that the first in-feed roller (40) and the last out-feed roller (70) of Lau et al. (see FIG. 2 thereof) do in fact apply undesirable bending forces or moments to the panels as they travel thereover, thereby resulting in significantly less than accurate strength and stiffness values for the tested panels. It has been determined according to the present invention that if the panels are subjected to a bending force outside the critical load zone or path, the deflection for a specific load or the load applied for a particular deflection may be greater than or less than what the actual deflection or load would be absent the undesirable bending force, depending on the direction the panels are caused to bend outside the load zone.

Another problem with Lau et al. concerns the location of the photo switches (1)–(4) (see FIG. 1 thereof) which communicate with the microprocessor (22) so that the microprocessor knows when to begin and when to end taking and recording loading and temperature readings for a specific panel traveling through the panel tester. Lau et al.

disclose that a composite panel (10) moves in an "S" shaped path through the tester. The first deflector roll (14) is positioned midway between a first pair of spaced positioning rolls (13) each of which cooperates with its respective reaction roll (50) to clamp the panel (10) therebetween, all of which function to bend the panel in a first direction in the first curved portion of the "S" shaped path. The second deflection roll (16) is positioned substantially midway between a second pair of positioning rolls (13) each of which cooperates with its respective reaction roll (60) to clamp the panel (10) therebetween, all of which function to bend the panel in a second direction opposite to the first direction in the second curved portion of the "S" shaped path, i.e., in a reverse curvature to that forced by the first deflection roll (14). According to Lau et al., when the photo switches indicate that a panel is in the tester, readings from the load cells (18) and temperature sensor (24) are taken at predetermined intervals and the microprocessor uses these readings to calculate a strength and stiffness value for each panel tested. As shown and described in Lau et al., the photo switches are placed along the processing line with no particular regard as to how their placement may affect the calculated strength and stiffness values. In other words, what Lau et al. fail to recognize, and what has been determined according to the present invention, is that the location of the photo switches or sensors relative to the load zone of the "S" shaped path is important in terms of the overall calculated strength and stiffness value for each panel tested.

According to the present invention, it has been determined that in order to compute more accurate strength and stiffness values for the panels, each panel should be subjected to bending forces in the first and second curved portions of the "S" shaped path or load zone between the pairs of opposed positioning and reaction rolls adjacent to the respective deflector rolls. Any forces or adverse bending moments applied to the panels outside the load zone which causes the panels to bend in an undesirable manner, will result in less than accurate strength and stiffness values. Accordingly, since the panels should only be subjected to the appropriate bending forces within the load zone, and since the microprocessor calculates a strength and stiffness value for each panel traveling through the panel tester, it is desirable for the microprocessor to take and record the desired measurement readings only when each panel is in or substantially in the load zone of the "S" shaped path as defined between the pairs of opposed positioning and reaction rolls. Locating the photo switches as illustrated in Lau et al. results in the microprocessor taking and recording the load and temperature readings for the panels when the panels are not properly in the defined load zone of the "S" shaped path, thereby undesirably skewing the calculated strength and stiffness values for the panels.

Yet another problem with Lau et al. is that the panel tester and grader does not provide a mechanism to measure the thickness of each panel tested with a high degree of accuracy. As explained in Lau et al., a thickness value for the panels is needed in order to calculate the strength and stiffness values for the panels. In the preferred embodiment of Lau et al., a nominal thickness value for a set of panels (see, e.g., TABLES I and II therein and the description thereof) is simply inputted into the microprocessor, so that the appropriate calculations can be made. As noted, Lau et al. do teach that if a more accurate calculation of strength and stiffness is desired, a thickness sensor such as a laser sensor or an ultrasonic sensor may be used to measure the actual thickness instead of using the nominal thickness of each panel. Even so, what Lau et al. fail to recognize, and what has been determined according to the present invention, is that the thickness of each panel is a very significant parameter in determining the most precise measure of the strength and stiffness value for each tested panel. For example, a laser sensor will only measure the thickness of a panel at the specific location where the laser contacts the panel. As can be appreciated by those skilled in the art, panels of the type described herein can have varying thicknesses over the length and width of each panel. A single laser sensor cannot take into account the varying thicknesses throughout the panels. As a result, the averaged thickness measurement obtained by a laser sensor may not be a true representative measurement of the overall thickness of the particular panel. It is possible that multiple laser sensors could be used to improve the accuracy of the averaged thickness measurement for each panel, but multiple sensors would add undesirable cost and complexity to the overall panel tester, thereby resulting in a less than optimum machine. Likewise, an ultrasonic sensor will simply not provide accurate thickness measurements. As can be appreciated by those skilled in the art, panels of the type described herein have a tendency to vibrate as they are processed along the continuously operating panel tester and grader. Such vibrations in the panels will undoubtedly adversely affect the readings taken by an ultrasonic thickness tester. Thus, according to the present invention, it has been determined that in order to obtain a more accurate calculated strength and stiffness value for each panel, a new and improved thickness measuring device is required.

In sum, what is needed is a panel tester and grader that improves on the apparatus and method described in Lau et al., thereby providing a more accurate account of the strength and stiffness properties of each panel tested.

SUMMARY OF THE INVENTION

The present invention provides a panel tester and grader that accomplishes the features described herein as well as other features while at the same time alleviating the noted problems and other problems of the prior art. In one aspect, the present invention is an improvement over the apparatus and method of Lau et al. The noted advantages and other advantages of the present invention are realized in one aspect thereof in a panel tester and grader which provides a fully automatic structural-use panel performance test and grade system, and which also provides timely and tamper-free quality control testing. As such, the panel tester and grader system hereof provides reliable strength and stiffness testing and grading of product quality, heretofore unheralded in the prior art. The system in accordance with the present invention is particularly suited for continuous non-destructive in-line testing of wood panels. The system automatically applies a load to panels to be tested, preferably to deflect each panel a predetermined amount, reads and records the load required to deflect each panel, measures the thickness and temperature of each panel, all without operator involvement, and provides a printout test report which includes a strength and stiffness value for each tested panel. The system is extremely cost effective to the manufacturer as well as the ultimate user. Savings are realized, for example, in the ability to correct quality performance problems directly after they arise, thereby getting the most value as well as quality out of the processed panels. If the panel tester and grader of the present invention identifies poor quality panels, adjustments can be made to the upstream panel processing equipment so as to improve the quality of the finished panel products, thereby enabling the overall panel making process to operate in an efficient and economical manner which ultimately contributes to the overall realized profits.

In one aspect, the present invention prevents or substantially minimizes unwanted bending forces from being applied to the panels as the panels travel through the panel tester and grader. Like Lau et al., the present invention imposes a double reverse bend or "S" shaped configuration on the panels as they pass through the conveyor at line speed, and the loads and the amount of deflection required to form this "S" shaped configuration are used to determine the strength and stiffness values of the panels. Like Lau et al., the panel tester and grader according to the present invention allows panels to be graded so rejects can be identified and panels can be separated into grade groups representing different strength and stiffness ranges. Like Lau et al., the panels may be tested at one temperature, approaching the press temperature, and the stiffness and strength values are determined for the end products at another temperature. There are other similarities between the present invention and Lau et al. which can be observed from a comparison of one to the other. However, as will be further explained below, there are many differences between the present invention and Lau et al. such as, for example, the manner in which the positioning and reaction rolls are located in a predetermined position prior to sending the panels therebetween. One particular difference between the present invention and Lau et al. resides in the elimination of the first in-feed roll and the last out-feed roll and the problems attributable thereto, so as to provide more accurate strength and stiffness values for the tested panels. As a result, according to one embodiment of the present invention, panels are fed to a pair of opposed positioning and reaction rolls which represent the beginning of the first curve of the "S" shaped path or the beginning of the load zone without substantially subjecting the panels to a premature bending force which, if present, could undesirably affect the overall strength and stiffness value for each panel. Additionally, the present invention allows the panels to exit out of the panel tester and grader from between a pair of opposed positioning and reaction rolls which represent the end of the second curve of the "S" shaped path or the end of the load zone without substantially subjecting the panels to an extra, unnecessary bending force which, if present, could also undesirably affect the strength and stiffness value for each panel.

In another aspect of the present invention, sensors are strategically positioned along the processing line to prevent or to substantially minimize the taking and recording of unwanted load and temperature readings by the microprocessor. As noted, panels move in an "S" shaped path through the panel tester and grader. A first load roll is positioned generally midway between a first pair of spaced positioning rolls each of which cooperates with a respective reaction roll to clamp each panel therebetween, all of which function to bend each panel in a first direction in a first curved portion of the "S" shaped path or load zone. A second load roll is positioned generally midway between a second pair of spaced positioning rolls each of which cooperates with a respective reaction roll to clamp each panel therebetween, all of which function to bend each panel in a second direction opposite the first direction in a second curved portion of the "S" shaped path or load zone. The positioning and reaction rolls are advantageously located one above the other such that a vertical or substantially vertical plane extends through the centers of the respective opposing rolls. The planes extending through the centers of the rolls define nip areas between the opposing rolls and further define the beginning and ending boundaries of the curved portions of the "S" shaped path or load zone. A feature of the present invention involves the taking and recording of the load and temperature measurements of each panel when the panels are traveling within or substantially within the load zone. Thus, according to the present invention, it is desirable to properly position the necessary sensors as close as is practically possible to the planes extending through the opposed positioning and reaction rolls, thereby, in effect, being as close as possible to the boundaries of the curved portions.

In one embodiment, the positioning and reaction rolls are mounted for rotation about respective shafts. Each roll contains a circular groove which is preferably located midway between the ends of the roll, and which preferably has a depth which extends through the outer surface of the roll to the outer surface of the shaft. The positioning rolls are located relative to its opposing reaction roll such that the grooves of the positioning rolls align with the grooves of the respective reaction rolls, thereby providing a channel extending between the outermost vertical peripheries for each set of opposed rolls. A plurality of sensors, one for each channel, are positioned along the processing path traveled by the panels such that each sensor emits a signal which travels through its complementary channel. In this way, as a panel traveling through the processing line breaks the plane of the signal of any particular sensor, that sensor sends a signal to the microprocessor indicating that the sensor plane has been broken, whereby the microprocessor knows whether or not a panel is properly within or substantially properly within the load zone of the "S" shaped path. The sensors and microprocessor are programmed to cooperate together such that the microprocessor begins taking and recording load and temperature readings when certain sensor planes are broken thereby indicating that a panel is properly within the load zone, and stops taking and recording load and temperature readings when the other sensor planes are broken thereby indicating that a panel is not properly within the load zone. Since the planes extending through the opposing positioning and reaction rolls represent the beginning and ending points of the curved portions of the "S" shaped path or load zone, and since the sensors pass sensing signals or mediums through the grooves or channels extending between the respective opposing rolls near the outer diameter of the shafts of the rolls, the load and temperature readings are only taken and recorded while the panels are substantially within the load zone. This is an improvement over the Lau et al. reference because, unlike Lau et al., the panel tester and grader according to the present invention includes sensors which are strategically placed along the panel processing line with respect to the load zone so as to communicate with a microprocessor in such a manner that prevents or substantially minimizes the taking of undesirable load and temperature readings. Contrary to the present invention, the photo switches of Lau et al. are located in areas far removed from the intended load zone of the "S" shaped path.

In a further aspect of the present invention, a panel thickness measuring device is positioned relative to the framework of the panel tester and grader in order to provide a more accurate measurement of the thickness of each panel as the panels are fed through the machine. As mentioned, the thickness of each panel contributes to the final calculated strength and stiffness value for each panel. Thus, the more accurate the thickness measurement is for each panel, the more accurate the strength and stiffness values will be for each panel. The positioning and reaction rolls are supported by suitable framework which may be moved in a vertical direction through connection with electro-mechanical actuators. The electro-mechanical actuators move the appropriate portions of the framework, thereby moving the rolls, into a preset position depending on the general thickness of the panels to be tested. Preferably, the gap between each pair of cooperating rolls will be slightly smaller than the thickness of the panels to be tested. The electro-mechanical actuators are preferably provided with spring mounts so that when a panel passes between the cooperating rolls, the actuators can absorb the difference in the thickness of each panel while maintaining the rolls in contact with the adjacent face of the panel being tested. Thus, at least portions of the framework has, in effect, a limited range of motion during operation which enables panels having varying thicknesses to pass through the machine so that the panels are not damaged when passing between the opposed sets of rolls. According to the present invention, a thickness measuring device such as a LVDT is coupled to the framework so as to be able to measure the distance between the cooperating sections of the framework as this distance varies, according to the thickness of each panel traveling through the machine. A thickness measuring device according to the prevent invention will pick up most, if not all, of the variations or aberrations of thickness in each panel to be tested. In this way, the microprocessor is able to calculate a more accurate averaged thickness measurement for each panel which will result in a more accurate overall strength and stiffness value.

In yet another aspect, the present invention provides a method of testing the strength and stiffness characteristics of panel-like materials comprising the steps of feeding each panel in an "S" shaped load zone between a plurality of pairs of rolls, deflecting each panel from both sides and measuring the deflection load for a deflection amount when the panel is substantially within the load zone, measuring the temperature of the panel being tested when each panel is substantially within the load zone, measuring the actual thickness of each panel when each panel is substantially within the load zone, providing a plurality of sensors which are strategically placed along the processing line which determine when each panel is substantially within the load zone and, preferably, calculating an end-use strength and stiffness value for each panel tested based on the load, deflection, temperature and thickness readings for each panel.

Other features and advantages of the invention will become apparent to those skilled in the art upon review of the following detailed description, claims and drawings in which like numerals are used to designate like features.

BRIEF DESCRIPTION OF THE DRAWINGS

FIG. 1 illustrates a side elevational view of certain components of a continuous panel tester and grader embodying the features of the present invention.

FIG. 2 is a view taken along line II—II of FIG. 1 illustrating one aspect of the present invention.

FIG. 3 is a view taken along line III—III of FIG. 1 illustrating another aspect of the present invention.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting.

DETAILED DESCRIPTION OF THE PREFERRED EMBODIMENTS

FIG. 1 illustrates an in-line panel tester and grader 10 wherein a composite panel 12 moves in an "S" shaped path. Since the present invention is intended to provide certain improvements over the apparatus and method described in Lau et al., a complete description regarding many of the details of the apparatus 10 is not needed. Reference can be made to Lau et al. for a more complete description of the nonessential components of the apparatus and method according to the present invention. However, it should be noted that, like Lau et al., it is envisioned that the present invention may mark the end-use stiffness and strength figures on each panel and the present invention may also grade panels identifying rejects which can be discarded. In addition, it is envisioned that the panels may be sorted out into different grade bins thereby identifying premium quality panels and lesser quality panels. Lau et al. describes one method of calculating an end-use strength and stiffness value for each tested panel which the present invention can employ. Moreover, as will be evident below, the present invention is also capable of use in other panel testing and grading systems wherein the end-use strength and stiffness value is based at least in part on the thickness of each panel and/or on the deflection for a specific load or the load for a particular deflection. As such, even though the present invention is described as having many improvements over Lau et al., it should be appreciated that the apparatus and method described herein is capable of use in other panel testers and graders according to the principles of the present invention. The present invention is directed toward improving the accuracy and reliability of data used to determine the end-use strength and stiffness value for each tested panel, such as, for example, the applied load for a particular deflection and the actual thickness for each panel. Thus, the present invention can be used in other situations where similar improvements are desired.

With reference to FIG. 1, a pair of cooperating in-feed guide rolls 14 and 18 guide the panel 12 past a first pair of spaced apart positioning rolls 22 each of which cooperate with a respective spaced apart reaction roll 26 to clamp the panel 12 therebetween and position the panel 12 against the reaction rolls 26. A first deflector roll 30 is positioned generally midway between the rolls 22 and functions to bend the panel 12 in a first direction into a first curved portion 34 of the "S" shaped path.

The panel 12 then passes and is guided by a second pair of spaced apart positioning rolls 38 each of which cooperates with a respective spaced apart reaction roll 42 to clamp the panel 12 therebetween. A second deflector roll 46 is positioned generally midway between the second pair of positioning rolls 38 and bends the panel 12 in a second direction opposite to the first direction in which the panel 12 is bent by deflector roll 30 and into the second curved portion 50 of the "S" shaped path, i.e., in a reverse curvature to that formed by the first deflector roll 30. The panel 12 then exits through a pair of cooperating out-feed guide rolls 54 and 58. The deflector rolls 30 and 46 each have a pair of load cells (not shown), one on each end, which sends a signal to further processing equipment corresponding to the amount of load being applied to the panel 12. The load cells may be any type of load cell commonly known to those skilled in the art which functions according to the principles of the present invention. A temperature sensor 60, which may be any suitable sensor known to those skilled in the art, senses the temperature of the panel 12 being tested and sends a signal to the further processing equipment which corresponds to the temperature of the panel 12 being tested.

The positioning of the guide rolls 14, 18, 54 and 58, positioning rolls 22 and 38, reaction rolls 26 and 42, and deflector rolls 30 and 46 are all suitably controlled by a computer or microprocessor (not shown) operatively connected thereto. The microprocessor suitably utilizes the information from the load cells, the temperature sensor, and the data concerning the make-up and size of each panel to calculate the end-use strength and stiffness properties for each panel as such is described, for example, in Lau et al. Such information may naturally be shown on a computer screen or printed by a printer (not shown). In any event, the microprocessor is of a suitable type which is capable of receiving, interpreting and analyzing the necessary information to output the desired results.

The panel tester and grader 10 includes a main frame 62 which has three subframes therein. A first loading frame 66 supports the first deflector roll 30 and the two lower positioning rolls 22. A second loading frame 70 supports the second deflector roll 46 and the two upper positioning rolls 38. A third subframe 74 supports the lower reaction rolls 42. The upper reaction rolls 26 are supported directly by the main frame 62.

The in-feed guide rolls 14 and 18 are supported by an "L" shaped arm 78 which is pivotally mounted on the axis of rotation 80 of the adjacent reaction roll 26. A second "L" shaped arm (not shown) is positioned at the other ends of the rolls 14 and 18, such that reference to one can be viewed as reference to the other. The angular position of the arm 78 is adjusted by an electro-mechanical actuator 82 which pivots the arm 78 about the axis 80 of roll 26. The position of arm 78 is preferably predetermined based on the intended travel path for the panel 12 through the machine 10. The microprocessor is operatively coupled to the actuator 82 for controlling the location of the arm 78. Although the actuator 82 may be one of many different types of actuators capable of performing the desired functions, a linear actuator sold under the name of Warner Electrak 100, by Warner Electric of South Beloit, Ill., is particularly well suited for use according to the principles of the present invention.

The bottom in-feed guide roll 18 is connected to an electro-mechanical actuator 86 having a spring mount. The spacing between the top in-feed guide roll 14 and its cooperating nip forming bottom in-feed roll 18 is adjusted by the electro-mechanical actuator 86 which moves roll 18 the required amount depending on the general thickness of the panel to be tested. The microprocessor is operatively coupled to the actuator 86 for controlling the location of the roll 18 relative to roll 14. As will be further explained below, the spring mount of the actuator 86 allows the cooperating rolls 14 and 18 to accommodate panels passing therebetween which are of varying thicknesses so as not to damage the panels. Although the actuator 86 may be one of many different types of actuators capable of performing the desired functions, a linear actuator like actuator 82, would work according to the present invention.

The position of arm 78 is determined in one aspect on the position of the first deflector roll 30 which determines the degree of bending of the panel 12 in the first curved position 34 of the "S" shaped path. The panel 12 passes over the pair of rolls 22 and is deformed by the roll 30 which causes the panel 12 to be pressed against the reaction rolls 26 thereby causing the panel 12 to bend. When the lead end of the panel 12 passes over roll 30, its direction of travel will not intersect with the nip formed between the next pair of cooperating rolls 22 and 26, thus a deflector 90 is provided to deflect the leading end of the panel 12 into the predetermined nip formed between the next pair of opposite rolls 22 and 26.

The first deflector roll 30 is mounted on the first loading frame 66 with an arm 94 which is pivotally mounted on the frame 66. The position of the roll 30 relative to the frame 66 in the vertical direction can be determined in any number of different ways, one such way being described, for example, in Lau et al. The roll 30 is generally positioned at a selected distance above the horizontal plane defined by the upper portions of the outer peripheries of the two spaced-apart rolls 22 so as to impose the desired degree of bending to the panel 12 being tested.

Electro-mechanical actuators 98 are supported by the main frame 62 and connected to the first loading frame 66. There are a total of four actuators 98, one for each corner of frame 66. The actuators 98 control the vertical movement of the frame 66 and are set depending on the general thickness of the panels to be tested to provide the desired gap between the rolls 22 and 26. The gap between each pair of cooperating rolls 22 and 26 should be slightly smaller than the thickness of the panel to be tested. The actuators 98 include spring mounts so that when a panel having varying thickness passes between the positioning rolls 22 and reaction rolls 26, the actuators 98 absorb the difference in the thickness of the panel while maintaining the rolls 22 and 26 in contact with the adjacent faces of the panel 12 being tested. It should be noted that when the general panel thickness for the panels to be tested is changed (e.g., from ½-inch panels to ⅞-inch panels), the position of the roll 30 (as well as roll 46) is changed so that the degree of deformation of the panel changes and the "S" shaped path is thus varied. Although the actuators 98 may be one of many different types of actuators capable of performing the desired functions, a stepper motor actuator sold under the part number EC2S32T-5004A-50-MSZ-MT1E, by Industrial Device Corporation of Novato, Calif., is particularly well suited for use according to the principles of the present invention.

The subframe 74 is moved up or down depending upon the required "S" shaped configuration by electro-mechanical actuators 102, although other suitable positioning devices may be employed. Actuators 102 are supported by the main frame 62 and connected to the subframe 74. There are a total of four actuators 102, one for each corner of the subframe 74. Actuators 102 are preferably of the same type as actuators 98 including the same type of spring mount system.

The second loading frame 70 is substantially the same as the first loading frame 66, but is inverted with the second deflector roll 46 pushing down on the panel between the two positioning rolls 38 which cooperate with reaction rolls 42. The second deflector roll 46 is mounted on frame 70 in much the same fashion as deflector roll 30 is mounted on frame 66. As shown, an electro-mechanical actuator 106 may be used independently or in connection with a step cam (not shown) to vertically maneuver the roll 46 with respect to frame 70, although the roll 46 may be positioned relative to the frame 70 in any number of different ways suitable for use with the present invention. Electro-mechanical actuators 110 are placed in each corner of frame 70 in order to move the frame 70 in a vertical direction. Such actuators 110 are like actuators 98 and 102. It will be apparent that because the roll 46 is beneath the frame 70, it will be mounted in a suitable manner to prevent it from falling out of position.

A deflector shoe 114, substantially equivalent to deflector 90, is provided to guide the panel 12 to the last positioning roll 38 in the second curved portion 50 in much the same way deflector 90 guides panel 12 to the last positioning roll 22 in the first curved portion 34.

The panel 12 passes from between the last positioning roll 38 and last reaction roll 42 and then from between the out-feed guide rolls 54 and 58. Guide rolls 54 and 58 are mounted on a pair of "L" shaped arms 118 (only one shown) in much the same way as in-feed guide rolls 14 and 18 are mounted on arms 78. Arm 118 is pivotally mounted on the axis of rotation 122 of the adjacent reaction roll 42. The angular position of the arm 118 is adjusted by an electro-mechanical actuator 126 which pivots the arm 118 around the axis 122 of roll 42. The position of arm 118 is preferably predetermined based on the intended travel path for the panel 12 through the machine 10. The microprocessor is operatively coupled to the actuator 126 for controlling the location of the arm 118. Actuator 126 is preferably of the same type as actuator 82. The top out-feed guide roll 54 is connected to an actuator 119, which is like actuator 86, and is operable much like the bottom in-feed guide roll 18 is operable.

As in Lau et al., during movement through the "S" shaped path, forces are applied to each panel by the deflector rolls 30 and 46 and their respective reaction rolls 26 and 42 against which the panel is positioned by the positioning rolls 22 and 38. The in-feed guide rolls 14 and 18 and the out-feed guide rolls 54 and 58 ensure that the panel 12 stays in its normal path or trajectory and does not exert any significant forces on the panel as this would distort the loading. Unlike Lau et al., the present invention eliminates the first in-feed roll (40) and last out-feed roll (70) to substantially ensure that there are no bending forces applied to the panel 12 outside of the "S" shaped load zone.

The actuators, in conjunction with the microprocessor, move the appropriate framework to position all of the rolls in a preset position based on the general size of the panels to be tested. Once the rolls are properly positioned, a panel is passed through the testing machine which will appropriately activate the load cells to measure the applied load for the particular deflection of the panel and the temperature sensor to sense the temperature. A thickness measuring device described below measures the thickness of each panel. The load, temperature and thickness values, among other things, are utilized by the microprocessor to determine the strength and stiffness value for each panel at ambient or end-use temperature. Lau et al. describes one algorithm which may be used to calculate such a value. Moreover, other algorithms may be used in accordance with the present invention.

FIG. 2 illustrates one aspect of the present invention in more detail. As previously explained, the location of the photo switches or sensors 130, 134, 138 and 142 (FIG. 1) is important in terms of determining when a panel is in the "S" shaped load zone so that a more accurate strength and stiffness value can be calculated. Although many different types of sensors may be employed, such as reflector-type sensors, typical pass through optical sensors are particularly suited for use according to the principles of the present invention.

As shown in FIG. 1, the positioning rolls 22 and 38 are located opposite their respective reaction rolls 26 and 42. In this manner, vertical or substantially vertical planes 146 (see FIG. 2) extend through the axis of rotation of each of the respective opposing rolls. The first curved portion 34 of the load zone of the "S" shaped path is defined by the vertical planes 146 extending through the positioning rolls 22 and their respective reaction rolls 26. The second curved portion 50 of the load zone of the "S" shaped path is defined by the vertical planes 146 extending through the positioning rolls 38 and their respective reaction rolls 42. As noted, a feature of the present invention involves the taking and recording of the load and temperature measurements of each panel when the panels are traveling within or substantially within the "S" shaped load zone.

As illustrated in FIG. 2, each positioning and reaction roll is mounted about a shaft 150 for rotation therewith. Each positioning and reaction roll includes a circular groove 154 which is preferably located midway between the ends of each roll and which preferably has a depth which extends through the outer surface 158 of each roll to the outer surface 160 of each shaft 150. The positioning rolls, such as positioning roll 22, are each located relative to its opposing reaction roll, such as reaction roll 26, such that the grooves 154 of the positioning rolls align with the grooves of the respective reaction rolls. Thus, as can be observed, a channel 162 extends between the outermost vertical peripheries for each set of opposed rolls. One of the sensors or emitters 130, 134, 138 and 142 and its respective reflector or receiver 166 is positioned in each channel 162 defined by the opposing rolls. Preferably, for reasons more fully explained below, the light-emitting source or sensing medium of each sensor is located ½ inch away from the outer surface 160 of the shaft 150.

The sensors communicate with the microprocessor as follows. When the front edge of the leading end of the panel 12 breaks the sensing beam or plane of the sensor 134, a signal is sent to the microprocessor indicating that the panel 12 is properly located in the first curved portion 34 of the load zone. Once the computer knows the panel is in the first portion of the load zone, it starts receiving and recording signals transmitted from the load cell of the deflector roll 30 corresponding to the load being applied to obtain a particular deflection, as well as signals from the temperature sensor 60. When the front edge of the leading end of the panel 12 breaks the sensing beam or plane of the sensor 142, a signal is sent to the microprocessor indicating that the panel 12 is located in the second curved position 50 of the load zone. Once the computer knows the panel is in the second portion of the load zone, it starts receiving and recording signals transmitted from the load cell of the deflector roll 46 corresponding to the load being applied to obtain a particular deflection, as well as signals from the temperature sensor 60. When the trailing edge of the back end of the panel 12 breaks the sensing beam or plane of the sensor 130, a signal is sent to the microprocessor indicating that the panel 12 is no longer properly in the first curved portion 34 of the load zone. Once the computer knows the panel 12 is not properly located in the first curved portion 34 of the load zone, it stops receiving and recording information concerning the load and temperature readings. When the trailing edge of the back end of the panel breaks the sensing beam or plane of the sensor 138, a signal is sent to the microprocessor indicating that the panel 12 is no longer properly in the second curved portion 50 of the load zone. Once the computer knows the panel 12 is not properly located in the second curved portion 50 of the load zone, it stops receiving and recording information concerning the load and temperature readings.

Various features of the invention are explained below by way of reference to the following exemplary example.

A tester and grader according to the present invention is configured to handle 4×8 feet panel sheets. The first and second curved portions have a dimension of thirty inches and the deflector rolls 30 and 46 would be located midway between the respective curved portions. The positioning rolls and reaction rolls each have a 4-inch diameter with 2-inch diameter shafts. The microprocessor does not begin receiving and recording load or temperature values for each panel until the sensing plane of the sensor 134 is broken. In this arrangement, load and temperature data would not be taken for the first 16.5-inches of the 96-inch panel sheet (i.e., the distance between the center of the deflector roll 30 and the appropriate vertical plane 146, plus ½ inch which is the preferred location of the sensing beam or plane from the outer surface of the shaft 150). Likewise, the microprocessor would stop receiving and recording load or temperature values for each panel when the sensing beam or plane of the sensor 138 is broken, thereby resulting in no load or temperature data for the last 16.5-inches of the 96-inch panel. Although the end-use strength and stiffness value of the panels is based only on data received for 62 out of the 96-inches of the panel, this is a tremendous improvement over what is shown in Lau et al. due to the location of the photo sensors therein.

Accordingly, locating the sensors as described herein greatly improves upon the overall strength and stiffness value for each tested panel because the microprocessor only takes and records data when the panels are properly located in the panel tester and grader.

FIG. 3 illustrates another aspect of the present invention in greater detail. As previously noted, a panel thickness measuring device 170 is positioned relative to the framework 70 and 74 in order to provide a more accurate measurement of the thickness of each panel as the panels are fed through the machine. Although the device 170 is shown in the second curved portion 50 (FIG. 1), it should be understood that the device 170 or a second device in addition to device 170 could be placed in the first curved portion 34.

The thickness measuring device comprises an LVDT 182 having a probe 186 and a cable 190, an "L" shaped plate 174 and a plate 178. LVDT's are commonly known and available from numerous commercial suppliers. Plates 174 and 178 may be a suitable material, but ¼-inch thick appropriately dimensioned aluminum plates would work well according to the principles of the subject invention.

Plate 174 is appropriately fastened to frame 70. Plate 178 is properly secured to frame 74. In addition, LVDT 182 is firmly attached to plate 178. The probe 186 is moved in and out of the cylindrical body of the LVDT due to its abutment against plate 174, as will be further explained below. Cable 190 provides the conduit for the signals being sent back and forth between the LVDT and the microprocessor for reasons which will be apparent below.

As explained, panel 12 travels between the positioning rolls and reaction rolls during the bending and loading process of the panel tester. When the panel 12 is located between the respective rolls, the gap between the opposing rolls is substantially equal to the thickness of the panels. This gap varies for each panel as the thickness of each panel varies. The spring-mounted actuators attached to the respective frames allow the gap to vary so the panels are not damaged as they pass between the opposing rolls. As the framework 70 moves up and down relative to the framework 74, the plate 174 will cause the probe 186 to move inward or allow it to move outward with respect to the body of the LVDT based on the thickness of the panel. The LVDT 182 sends a signal to the microprocessor corresponding to the thickness values of each panel. Preferably, there is an LVDT 182 on each side of the machine 10 to provide a better account for the panel thickness. The LVDT 182 takes two thickness readings at any given instant in time which the computer then averages for a single value. The LVDT 182 continuously measure the thickness of each panel so long as the panel is within one or both curved portions of the load zone as determined by the sensors 130, 134, 138 and 142. The microprocessor will record all of the thickness measurements and then average the measurements to obtain a single thickness value which is used by the microprocessor in computing the actual end-use strength and stiffness value.

The device 170 provides a more accurate measure of the thickness of each panel 12, thereby providing a more accurate strength and stiffness value as compared to prior devices. The device 170 is capable of picking up most, if not all, of the variations or aberrations in a panel which could affect the average thickness value for each panel.

The foregoing description of the present invention has been presented for purposes of illustration and description. Furthermore, the description is not intended to limit the invention in the form disclosed herein. Consequently, variations and modifications commensurate with the above teachings in skill or knowledge of the relevant art, are within the scope of the present invention. The embodiments described herein are further intended to explain the best modes known for practicing the invention and to enable others skilled in the art to utilize the invention as such, or other embodiments and with various modifications required by the particular applications or uses of the present invention. It is intended that the appended claims are to be construed to include alternative embodiments to the extent permitted by the prior art.

Various features of the invention are set forth in the following claims.

What is claimed is:

1. A panel tester for a panel which moves in a path through said panel tester, comprising:
    a first roller disposed above the path, said first roller including an outer surface and a first circumferential groove around said outer surface;
    a second roller disposed below the path spaced apart and opposite said first roller, said second roller including an outer surface and a second circumferential groove around said outer surface, such that said first groove is aligned with said second groove to define a channel which extends through said rolls; and
    a location sensor positioned proximate to said channel for emitting a sensing medium through said channel and transmitting a position indicative signal corresponding to the position of the panel along the path.

2. A panel tester according to claim 1, wherein each of said rollers is mounted about a respective shaft for rotation therewith and wherein each of said grooves has a respective depth which extends from said outer surface of said rollers to an outer surface of said shafts.

3. A panel tester according to claim 1, wherein said sensing medium defined as a beam, travels through said channel at a distance of approximately ½ inch away from said outer surfaces of said shafts.

4. A continuous panel tester for determining desired performance properties of a panel moving in an "S" shaped path through said panel tester wherein the panel moves over a first deflector roll located between a first pair of spaced apart positioning rolls each of which cooperates with a respective reaction roll to clamp the panel therebetween in order to bend the panel in a first direction in a first curved portion of said "S" shaped path, and over a second deflector roll located between a second pair of spaced apart positioning rolls each of which cooperates with a respective reaction roll to clamp the panel therebetween in order to bend the panel in a second direction opposite said first direction in a second curved portion of said "S" shaped path, wherein each of said positioning rolls and their cooperating reaction rolls includes an outer surface and a circumferential groove extending around said outer surface, such that each cooperating pair of positioning and reaction rolls defines a channel which extends through said cooperating rolls, and wherein said panel tester further includes a plurality of location sensors positioned proximate to a respective channel for emitting a sensing medium through each of the respective channels and transmitting a position indicative signal corresponding to the position of the panel along said path, wherein the location of the panel is used in the determination of the desired properties of the panel.

5. A panel tester according to claim 4, wherein each of said rolls is mounted about a shaft for rotation therewith and wherein each of said grooves has a depth which extends from said outer surface of said roll to an outer surface of said shaft.

6. A panel tester according to claim 4, wherein said sensors are positioned proximate to said channels such that said sensing mediums defined as beams, travel through said channels at a distance of approximately ½ inch away from said outer surfaces of said shafts.

7. A panel tester according to claim 4, wherein each roll includes an axis of rotation and, wherein each pair of said cooperating positioning rolls and reaction rolls of said first pair of spaced positioning rolls and their respective reaction rolls includes a plane extending through said axes of rotation thereby defining said first curved portion or a first load zone of said "S" shaped path and, wherein each pair of said cooperating positioning and reaction rolls of said second pair of spaced positioning rolls and their respective reaction rolls includes a plane extending through said axes of rotation thereby defining said second curved portion or a second load zone of said "S" shaped path, whereby said first sensor of said plurality of sensors is placed upstream of said plane extending between said first pair of said cooperating positioning and reaction rolls located farthest to one end of the path, and whereby said second sensor of said plurality of sensors is placed downstream of said plane extending between said second pair of said cooperating positioning and reaction rolls located next in line along the path relative to said first pair of said cooperating positioning and reaction rolls and, whereby said third sensor of said plurality of sensors is placed upstream of said plane extending between said third pair of cooperating positioning and reaction rolls located next in line along the path relative to said second pair of said cooperating positioning and reaction rolls and, whereby said fourth of said plurality of sensors is placed downstream of said plane extending between said fourth pair of cooperating positioning and reacting rolls located farthest to the other end of the path.

8. A panel tester according to claim 7, wherein when a leading edge of the panel breaks said sensing medium of said second sensor, said corresponding sensor transmits a signal indicating that the panel is in a location along the path which signals that desired parameter readings of the panel may be taken in order to provide data for the determination of the desired properties and, wherein when a trailing edge of the panel breaks said sensing medium of said third sensor, said corresponding sensor transmits a signal indicating that the panel is in a location along the path which signals that no further parameter readings for the panel used for the determination of the desired properties should be taken.

9. A panel tester according to claim 8, wherein said first and second sensors determine when the panel is in the first load zone of said panel tester and, wherein said third and fourth sensors determine when the panel is in the second load zone of said panel tester.

10. A panel tester according to claim 4, wherein said panel tester does not include any additional rolls along the path which would subject the panel to undesired bending forces.

11. A panel tester for a panel moving in a path extending therethrough, comprising:

a first frame member, a second frame member disposed below said first frame member, a first roll, a second roll and a thickness measuring device;

said first roll supported on said first frame member above the path;

said second roll supported on said second frame member below the path and opposite said first roll;

said first frame and said second frame disposed such that said first roll and said second roll are proximate one another to define a gap therebetween for the panel to pass therethrough;

at least one of said first frame member and said second frame member being movable with respect to the other, said gap varying in distance corresponding to the thickness of the panel passing therethrough; and said thickness measuring device operatively coupled to said first frame member and said second frame member for measuring the distance of said gap.

12. An apparatus for determining the strength and stiffness of a panel moving along an "S" shaped path comprising:

a main frame;

a first load frame movably mounted on said main frame;

a first deflector roll adjustably mounted on said first load frame;

a first pair of positioning rolls mounted on said first load frame, each roll being positioned on opposite sides of said first deflector roll, and each positioning roll including a circular groove extending around an outer surface thereof;

a first pair of reaction rolls mounted on said main frame each forming a nip with an opposite one of said first pair of positioning rolls, and each reaction roll including a circular groove extending around an outer surface thereof;

wherein said grooves of said opposing first pairs of positioning and reaction rolls are aligned to define a channel extending through said opposed positioning and reaction rolls;

wherein said first deflector roll cooperates with said first pair of reaction rolls to bend the panel in a first direction of a first curved portion of the "S" shaped path;

a second load frame movably mounted on said main frame;

a second deflector roll adjustably mounted on said second load frame;

a second pair of positioning rolls mounted on said second load frame, each roll being positioned on opposite sides of said second deflector roll, and each positioning roll including a circular groove extending around an outer surface thereof;

a subframe adjustably mounted on said main frame;

a second pair of reaction rolls mounted on said subframe each forming a nip with an opposite one of said second pair of positioning rolls, and each reaction roll including a circular groove around an outer surface thereof;

wherein said grooves of said opposing second pairs of positioning and reaction rolls are aligned to define a channel extending through said opposed positioning and reaction rolls;

wherein said second deflector roll cooperates with said second pair of reaction rolls to bend the panel in a second direction opposite to said first direction in a second curved portion of the "S" shaped path;

a plurality of location sensor devices wherein a separate sensor is positioned within a separate one of said channels, wherein said sensor devices determine when the panel is completely within one or both of the curved portions of the "S" shaped path, which information is useful in determining the strength and stiffness value for the panel; and a thickness measuring device coupled to two of said frames so as to measure a distance between said frames, said distance changing as the panel travels through said panel tester if the panel has varying thicknesses, such information also being useful in determining the strength and stiffness for the panel.

13. A panel tester according to claim 12, wherein the movable frames are connected to at least one linear actuator each of which includes a spring mount which is adapted to absorb the difference in the thickness of the panel traveling through said panel tester.

14. A panel tester according to claim 12, wherein said thickness measuring device includes a movable probe and, wherein one of said frames supports said thickness measuring device, and wherein said probe abuts a portion of another of said frames such that as said gap varies, said probe moves in and out thereby measuring the size of said gap which correlates to the thickness of each panel and, wherein said panel tester includes a second thickness measuring device substantially similar to said first thickness measuring device, wherein each thickness measuring device is located on opposite sides of the panel.

15. A method of testing the strength and stiffness characteristics of a panel, comprising the steps of:

feeding each panel in an "S" shaped path having two load zones defined between a respective plurality of pairs of rolls, wherein said rolls are supported by at least two frame members in which at least one of said frame members is movable with respect to said other frame member;

deflecting each panel from both sides and measuring an applied load for a deflection amount when the panel is substantially within one or both of said load zones;

measuring a distance between said frame members, said distance changing as the panel travels along the "S" shaped path if the panel has a varying thickness;

providing a plurality of location sensors which are strategically placed along the "S" shaped path which determine when the panel is substantially within one or both of said load zones, said sensors being located near said pairs of rolls such that a sensing medium of each sensor travels through said adjacent pairs of rolls; and calculating an end strength and stiffness value for the panel using the load measurements and distance measurements.

* * * * *